United States Patent [19]
Breitschuh et al.

[11] Patent Number: 5,883,283
[45] Date of Patent: Mar. 16, 1999

[54] PROCESS FOR THE PREPARATION OF SUBSTITUTED 3-AMINOBENZONITRILES

[75] Inventors: Richard Breitschuh, Berlin, Germany; Benoît Pugin, Münchenstein, Switzerland; Adriano Indolese, Möhlin, Switzerland; Verena Gisin, Ueken, Switzerland

[73] Assignee: Novartis Finance Corporation, New York, N.Y.

[21] Appl. No.: 817,858

[22] PCT Filed: Oct. 5, 1995

[86] PCT No.: PCT/EP95/03936

§ 371 Date: Aug. 1, 1997

§ 102(e) Date: Aug. 1, 1997

[87] PCT Pub. No.: WO96/11906

PCT Pub. Date: Apr. 25, 1996

[30] Foreign Application Priority Data

Oct. 17, 1994 [CH] Switzerland .......................... 3121/94
Jun. 13, 1995 [CH] Switzerland .......................... 1743/95
Jul. 21, 1995 [CH] Switzerland .......................... 2156/95

[51] Int. Cl.$^6$ .......................... C07C 255/50; C07C 255/58
[52] U.S. Cl. .......................... 558/418; 558/414; 558/423
[58] Field of Search .......................... 558/418, 414, 558/423

[56] References Cited

PUBLICATIONS

Harris, Neil V. et al., Antifolate and Antibacterial Activities of 5–Substituted 2,4–Diaminoquinazolines, J. Med. Chem. vol. 33, 434–444, Dec. 1990.

*Primary Examiner*—Johann Richter
*Assistant Examiner*—Dominic Keating
*Attorney, Agent, or Firm*—Hesna J. Pfeiffer

[57] ABSTRACT

The invention relates to a process for the preparation of substituted 3-amninobenzonitriles, which comprises reacting the appropriate substituted 3-aminochlorobenzene with a cyano-donating reagent, and to the compounds thereby produced. The compounds are intermediates, which after further reaction, produce 1,2,3-benzothiadiazole-derivatives having plant immunizing properties.

19 Claims, No Drawings

PROCESS FOR THE PREPARATION OF SUBSTITUTED 3-AMINOBENZONITRILES

This application is a 371 of PCT/EP95/03936 Oct. 5, 1995.

The invention relates to a process for the preparation of substituted 3-aminobenzonitriles of the formula I

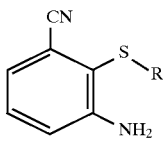

in which:
R is hydrogen or $C_1$–$C_{12}$alkyl, $C_3$–$C_8$cycloalkyl, $COR_1$, $C_1$–$C_8$alkoxyalkyl,
$C_1$–$C_6$hydroxyalkyl, $C_1$–$C_8$aminoalkyl, $C_1$–$C_8$alkyl-NH($C_1$–$C_4$alkyl),
$C_1$–$C_8$alkyl-N($C_1$–$C_4$alkyl)$_2$, substituted or unsubstituted benzyl; and
$R_1$ is $C_1$–$C_8$alkyl, $C_3$–$C_8$cycloalkyl or phenyl;
which comprises reacting, in a solvent at above 30° C., a substituted 3-aminochlorobenzene of the formula II

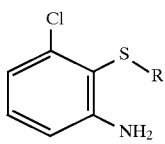

in which R is as defined for formula I with a cyano-donating reagent selected from amongst
a) CuCN or potassium cyanoferrate(II) (=$K_4$[Fe(CN)$_6$]) or calcium cyanoferrate(II) (=$Ca_2$[Fe(CN)$_6$]), in the presence of a complexing agent; or
b) any Cu(I) salt together with an alkali metal cyanide in the presence of a complexing agent; or
c) alkali metal cyanide, HCN, Ni(CN)$_2$ or tetramethylsilyl cyanide, or ketone HCN adduct or aldehyde HCN adduct, in the presence of a catalyst $M_3[Co^+(CN)_4]^{3-}$, or Pd°—$L_n$ or preferably [a nickel catalyst] Ni°—$L_n$ or a three-way mixture composed of NiL$_2$Hal$_2$, excess L and a reducing agent, M being an alkali metal, L being a ligand and n being 2 to 4.

The general terms used hereinabove and hereinbelow have the following meanings, unless otherwise defined:

alkyl groups are straight-chain or branched, depending on the number of carbon atoms, and are, for example, methyl, ethyl, n-propyl, isopropyl, n-butyl, sec-butyl, isobutyl, tert-butyl, sec-amyl, tert-amyl, 1-hexyl or 3-hexyl.

Depending on the size of the ring, cycloalkyl is cyclopropyl, cyclobutyl, cyclopentyl, cyclohexyl, cycloheptyl or cyclooctyl.

The ligands are phosphine groups PQ$_3$ in which
Q is $C_1$–$C_8$alkyl, $C_3$–$C_8$cycloalkyl, unsubstituted aryl or aryl which is substituted by
$C_1$–$C_8$alkyl, $C_1$–$C_4$hydroxyalkyl, $C_1$–$C_6$alkoxy, di($C_1$–$C_4$alkyl)amino($C_1$–$C_4$)alkyl, fluorine, SO$_3$H or N($C_1$–$C_4$alkyl)$_2$; or the ligands are
Q$_2$P—W—PQ$_2$ in which W is $C_1$–$C_8$alkyl or unsubstituted ferrocenyl or ferrocenyl which is substituted by one of the radicals mentioned for "aryl". Preferred ferrocenyl ligands are the unsubstituted ferrocenyl and the asymetrical monosubstituted representatives, for example 1-hydroxyethylferrocene and 1-dimethylaminoethylferrocene. Preferred catalysts are those of the formula Ni°—$L_n$ in which L is triphenylphosphine and n is 2 to 4, or those of the formula Ni°—$L_2$ in which L is (1,1'-bisdiphenylphosphine-1-(dimethylaminoethyl)ferrocene).

The compounds of the formula I are important intermediates in the preparation of the compound of the formula III and of its acid derivatives which have been disclosed as plant immunization agents and plant conditioners (cf. EP-B-313 512).

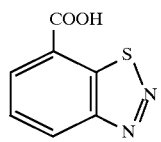

The process according to the invention comprises reacting a substituted 3-aminochlorobenzene of the formula II with a cyanide to give the compounds of the formula I according to the invention:

a) and b) [for example CuCN/pyridine or 3-methylpyridine/200° C.]

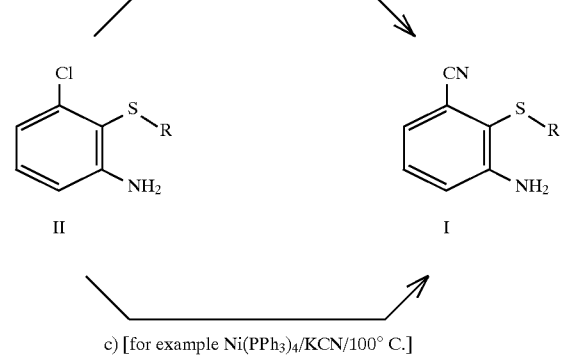

c) [for example Ni(PPh$_3$)$_4$/KCN/100° C.]

The exchange of halogen for the cyano group on aromatic compounds by CuCN or by complex metal cyanides, for example potassium cyanoferrate(II) (=$K_4$[Fe(CN)$_6$]) or calcium cyanoferrate (II) (=$Ca_2$[Fe(CN)$_6$]) in the presence of pyridine is known ("Rosenmund-von Braun synthesis"; for example Houben-Weyl, Methoden der organischen Chemie [Methods of Organic Chemistry], Vol. VIII, p. 302–3; Vol. E5, p. 1463–5, 1985).

It is also known that aromatically bonded halides can be replaced by the cyano group by means of a cyano-donating compound, for example alkali metal cyanide, HCN, Ni(CN)$_2$ or tetramethylsilyl cyanide, or ketone HCN adduct or aldehyde HCN adduct, in the presence of a Co, Pd or Ni catalyst (for example "Homogeneous Catalysis II" Adv. Chem. Ser. 132 ACS 1974 p. 252; Coll. Czechoslovak Chemm. Commun. Vol. 48 (1983) p. 1765).

The conversion of sulfur-containing chloroanilins with the specific 1,2,3 arrangement into the desired nitriles is novel. The surprising aspect is that this reaction proceeds with good selectivity and a high yield without substantial cleavage of a carbon-sulfur bond being observed. Moreover, it could not have been expected that this reaction proceeds readily in an electron-rich system (both the sulfur and the amino group on the phenyl ring are electron-donating substituents). It is furthermore surprising that even large groups, for example tert-butylthio, isopropylthio and cyclohexylthio, in the ortho-position relative to the reaction centre do not impede the reaction to a considerable extent.

Reactions a) and b) are carried out in the presence of a complexing agent.

This complexing agent causes on the one hand an acceleration of the Cl/CN exchange reaction, and, on the other hand, suppresses cleavage of the S—R bond.

The complexing agent is a nitrogen-containing, electron-donating compound, for example pyridine, quinoline or isoquinoline, which are unsubstituted or mono- to trisubstituted by $C_1$–$C_4$alkyl, $C_1$–$C_4$alkoxy, amino, $C_1$–$C_4$alkylamino or ($C_1$–$C_4$alkyl)$_2$amino. Particularly suitable as complexing agents are pyridine which is unsubstituted or mono- to trisubstituted by methyl, and quinoline; very particularly pyridine and 3-methylpyridine.

In a particular embodiment, the reaction is carried out with a) an equimolar (based on II) amount of CuCN or potassium cyanoferrate(II) (=$K_4$[Fe(CN)$_6$]) or calcium cyanoferrate(II) (=$Ca_2$[Fe(CN)$_6$]), in the presence of pyridine, methylpyridine, dimethylpyridine, trimethylpyridine, quinoline, dimethylaniline, acetonitrile, DMSO, benzonitrile, DMF or tetramethylurea; or b) any Cu(I) salt together with at least equimolar or greater (based on II) amounts of alkali metal cyanide, in the presence of pyridine, methylpyridine, dimethylpyridine, trimethylpyridine, quinoline, dimethylaniline, acetonitrile, DMSO, benzonitrile, DMF or tetramethylurea; or c) at least equimolar (based on II) amounts of alkali metal cyanide, HCN, Ni(CN)$_2$ or tetramethylsilyl cyanide, or keton HCN adduct or aldehyde HCN adduct, in the presence of a catalyst $M_3[Co^+(CN)_4]^{3-}$, or Pd$°$—$L_n$ or, preferably, Ni$°$—$L_n$, or a three-way mixture composed of NiL$_2$Hal$_2$, excess L and a reducing agent, M being an alkali metal, L a ligand and n 2 to 4.

Solvents which are advantageously used are aprotic polar solvents, for example dioxane, dimethylformamide, dimethylacetamide, N-methylpyrrolidone, dimethyl sulfoxide, acetonitrile, benzonitrile, tetramethylurea, hexamethylphosphoric triamide. In a preferred embodiment, at least equimolar amounts of the complexing agent, based on Cu or Fe, are used directly as the solvent; particularly preferred are pyridine and 3-methylpyridine, 3-methylpyridine being very particularly preferred because its high boiling point allows the process to be carried out under atmospheric pressure even at high temperature.

The reaction is carried out at temperatures between 50° and 350° C., preferably at temperatures between 150° and 250° C. As a rule, the reaction is carried out under atmospheric pressure or slightly elevated pressure (20 bar), preferably under atmospheric pressure up to 10 bar.

After a reaction time of approximately 3 to 18 hours, the yield of compounds of the formula I is up to 75% of theory, while the reaction rate is 80%, which corresponds to a yield of over 90% based on reacted educt.

Reaction a) with the use of CuCN is preferred.

Work-up is carried out for example as follows: Na$_2$S or NaCN, if desired in the form of an aqueous solution, is added to the reaction mixture, the mixture is then diluted with a solvent, for example ethyl acetate or methyl ethyl ketone (MEK) to make filtration easier, the salts are filtered off, the filtrate is evaporated, and the residue is purified either by distillation or by crystallization. If NaCN is used, the filtration gives directly reusable CuCN.

In reaction c), the exchange of chlorine for cyano is carried out in the presence of a catalyst.

The reaction can be carried out in nitriles (acetonitrile, benzonitrile), hydrocarbons, in particular aromatics, furthermore in ketones, alcohols (ethanol), water, amides (dimethylformamide=DMF), ethers or mixtures of these, preferably in DMF. The reaction temperatures are between 30° and 150° C., preferably 40° to 100° C. The catalytic action can be improved by reductive regeneration of the catalyst during the reaction. This regeneration is effected electrochemically or by adding a reducing agent. The yields in this variant are even higher than 90%, and the crude mixture can be reacted further directly for obtaining the benzothiadiazole-7-carboxylic acid III without isolating an intermediate.

The catalyst is prepared by known methods, for example EP-384 392, "Homogeneous Catalysis II" Adv. Chem. Ser. 132 ACS 1974 p. 252; J. Organomet. Chem. 173 (1979) p. 335, J. Organomet. Chem. 243 (1983) p. 95; Coll. Czechoslovak Chemm. Commun. Vol. 48 (1983) p. 1765. The preferred catalyst nickel tetrakistriphenylphosphine is prepared from nickel chloride hydrate, triphenylphosphine and a reducing agent. The reducing agents used are metals, for example Mn, Zn, Mg or Al in the form of shavings or powder; hydrides, for example sodium borohydride, lithium aluminium hydride or sodium hydride, or else electrochemical methods. The catalyst can be added to the reaction mixture, but it is preferably prepared in situ.

A further advantage of process a, b or c is that, after the further reaction which gives the benzothiadiazole-7-carboxylic acid of the formula III, the unreacted educt II is converted into the corresponding 7-chlorobenzothiadiazoles. Such 7-chlorobenzothiadiazoles can be removed readily from the mixture with the compound of the formula III by means of simple phase separation (water/organic solvent).

The invention also relates to the use of compounds of the formula I for obtaining the compound of the formula III.

These compounds can therefore be prepared from 2,3-dichloronitrobenzene, which is known, following equation I below:

Equation 1

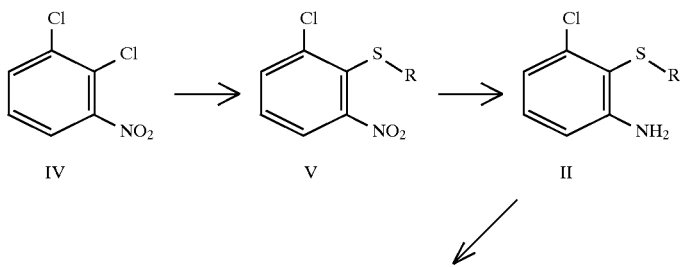

IV    V    II

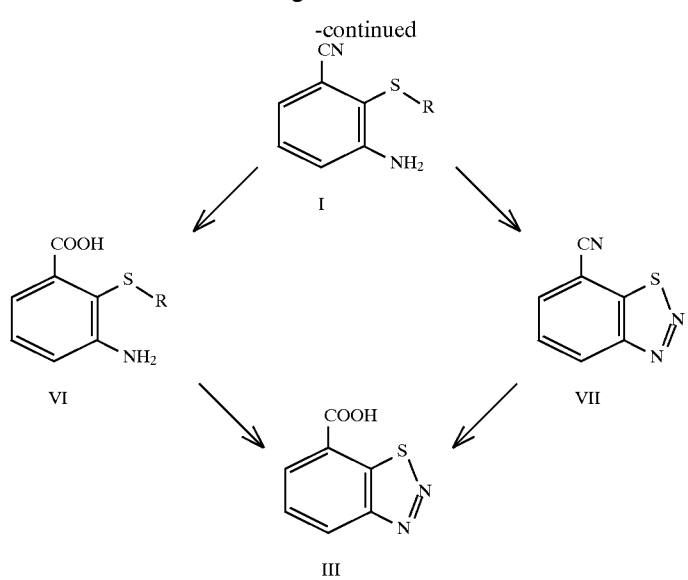

The reaction of 2,3-dichloronitrobenzene, of the formula IV, with a compound HS-R in which R is as defined above under basic conditions results in a specific exchange of the chlorine atom in the 2-position for an R-S radical to give a compound of the formula V; reduction of the nitro group to the amino group results in a compound of the formula II. The reduction is carried out by methods known per se, for example by Béchamp reduction using iron/hydrogen chloride, catalytic hydrogenation (Pd or Raney nickel) or by $Na_2S$ reduction.

The resulting compound of the formula II is converted into one of the compounds of the formula I by means of exchanging Cl for CN as described above. Diazotizing and cyclizing compounds of the formula I in subsequent steps results in the compound of the formula VII, from which the compound of the formula III is obtained by hydrolysing the cyano group to the carboxyl group, or from which the corresponding carboxamide is obtained by partial hydrolysis. Alternatively, if the sequence is reversed, hydrolysis of the cyano group in compounds of the formula I will give carboxylic acids or, if desired, carboxamides, of the formula VI, from which compound III can be obtained by diazotization. The diazotization is carried out by customary methods, for example with nitrous acid (=HONO) or with an inorganic or organic nitrite. Examples which may be mentioned are $NaNO_2$ or alkyl nitrite having up to 8 carbon atoms. The acid or alkaline hydrolysis of the nitrile group in the compounds I or VII is also carried out by customary methods, for example using concentrated sulfuric acid, hydrochloric acid or alkali metal oxides, alkali metal hydroxides, alkaline earth metal oxides or alkaline earth metal hydroxides, for example using NaOH or KOH.

The invention therefore also provides the process for the preparation of benzothiadiazole-7-carboxylic acid III from compounds of the formula II via 3-aminobenzonitriles of the formula I by means of a) exchange of Cl for CN to give a 3-aminobenzonitrile of the formula I as described above, and furthermore either b 1) hydrolysis of the cyano group to give a compound of the formula VI followed by diazotization of the amino group using nitrous acid or nitrite, with cyclization, to give a compound of the formula III; or b2) diazotization of the amino group using nitrous acid or nitrite, with cyclization, to give a compound of the formula VII, followed by hydrolysis of the cyano group to give a compound of the formula III.

The process is preferably carried out using compounds in which R is $sec\text{-}C_3\text{-}C_6$alkyl, $tert\text{-}C_4\text{-}C_6$alkyl or $C_5\text{-}C_6$cycloalkyl, particularly preferably isopropyl, tert-butyl or cyclohexyl.

The cyclization reaction to the benzothiadiazole can be carried out either at the cyanide level (I), the carboxamide level (IA) or the carboxylic acid level (VI), in accordance with equation 2.

Equation 2

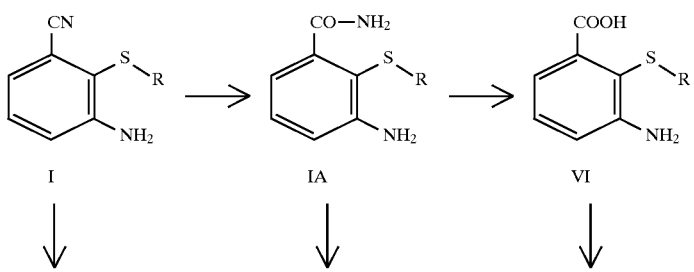

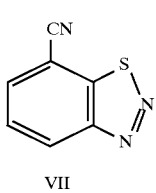

VII

VIIA

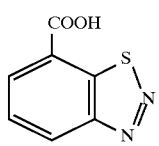

III

The process for the preparation of a compound of the formula XI

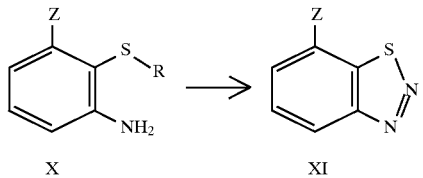

in which Z is CN, CO—NH2 or COOH comprises diazotizing a compound of the formula X in which Z and R are as defined above using nitrous acid or nitrite and subsequently cyclizing the product and is thus also provided by the invention.

The process is preferably carried out using compounds in which R is sec-$C_3$–$C_6$alkyl, tert-$C_4$–$C_6$alkyl or $C_5$–$C_6$cycloalkyl, particularly preferably isopropyl, tert-butyl or cyclohexyl.

The conversion of the compound of the formula IV into compounds of the formula V and reduction thereof to give a compound of the formula II in accordance with equation 3 is known in principle.

Equation 3

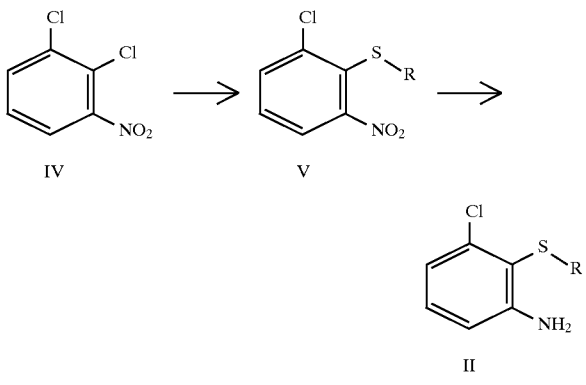

It has now been found that compounds of the formula II can be prepared in particularly high yield and purity when a) 2,3-dichloronitrobenzene, of the formula IV, and a compound HS-R in which R is as defined above are reacted in aqueous base in the presence of a phase transfer catalyst at 30° to 120° C. to give a compound of the formula V; after the reaction, the product is extracted by washing with a polar solvent, for example an alcohol, such as isopropanol or butanol, and subsequently washed with dilute acid, for example hydrochloric acid, to a pH of 5–7, and b) the reaction of the nitro group with hydrogen/Raney nickel is carried out in an alcohol or in water or in a mixture of these.

Using the compound of the formula V which has been prepared and purified as described under a), the reduction of the nitro group with Raney nickel proceeds surprisingly rapidly and requires only a small amount of catalyst; this avoids dangerous accumulation of readily degradable hydroxylamines, which is a considerable improvement from the point of view of security.

The invention therefore also provides the above-described processes for the preparation of a compound of the formula V from a compound of the formula IV, the preparation of a compound of the formula II from a compound of the formula V, and the two-step process for the preparation of a compound of the formula II from the compound of the formula IV via a compound of the formula V in which R is as defined above.

Novel and also provided by the invention are the compounds of the formula I

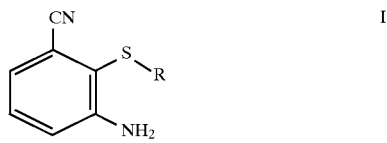

in which R is hydrogen, $C_1$–$C_{12}$alkyl, $C_3$–$C_8$cycloalkyl, $COR_1$, $C_1$–$C_8$alkoxyalkyl,
$C_1$–$C_6$hydroxyalkyl, $C_1$–$C_8$aminoalkyl, $C_1$–$C_8$alkyl-NH($C_1$–$C_4$alkyl),
$C_1$–$C_8$alkyl-N($C_1$–$C_4$alkyl)$_2$ or substituted or unsubstituted benzyl, and $R_1$ is $C_1$–$C_8$alkyl,
$C_3$–$C_8$cycloalkyl or phenyl.

Preferred compounds of the formula I are those in which R is sec-$C_3$–$C_6$alkyl, tert-$C_4$–$C_6$alkyl or $C_5$–$C_6$cycloalkyl, particularly preferably isopropyl, tert-butyl or cyclohexyl.

Novel and also provided by the invention are the compounds of the formula V

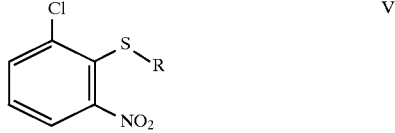

in which R is as defined for formula I, with the exception of hydrogen, methyl and substituted or unsubstituted benzyl; R is preferably sec-$C_3$–$C_6$alkyl or tert-$C_4$–$C_6$alkyl or $C_5$–$C_6$cycloalkyl, particularly preferably isopropyl or tert-butyl or cyclohexyl.

Novel and also provided by the invention are the compounds of the formula II

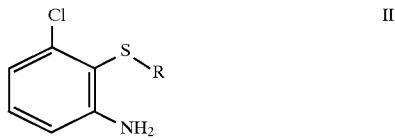

in which R is as defined for formula I, with the exception of hydrogen, methyl, ethyl and substituted or unsubstituted benzyl; R is preferably sec-$C_3$–$C_6$alkyl or tert-$C_4$–$C_6$alkyl or $C_5$–$C_6$cycloalkyl, particularly preferably isopropyl or tert-butyl or cyclohexyl.

Novel and also provided by the invention are the compounds of the formula IA

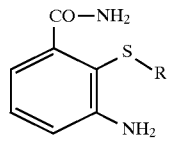

IA in which R is as defined for formula I; R is preferably sec-$C_3$–$C_6$alkyl or tert-$C_4$–$C_6$alkyl or $C_5$–$C_6$cycloalkyl, particularly preferably isopropyl or tert-butyl or cyclohexyl.

Novel and also provided by the invention are the compounds of the formula VI

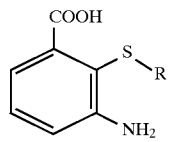

VI in which R is as defined for formula I, with the exception of substituted or unsubstituted benzyl; R is preferably sec-$C_3$–$C_6$alkyl or tert-$C_4$–$C_6$alkyl or $C_5$–$C_6$cycloalkyl, particularly preferably isopropyl or tert-butyl or cyclohexyl.

Preparation Examples

Example H-1

Prior-art process

Preparation of

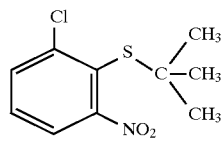

124.4 g of potassium carbonate and 144 g of 1,2-dichloro-3-nitrobenzene are introduced into 400 g of dimethylacetamide and the mixture is heated at 77° C. At this temperature, 72.2 g of tert-butylmercaptan are added dropwise in the course of 1 hour. The mixture is subsequently stirred at 100° C. for 2 hours. The reaction mixture is concentrated at 75° C. under a slight vacuum, 500 ml of water are added, and the end product is subsequently separated off at 60° C. This gives 185.5 g of the product of m.p. 50° C. (yield>95%).

Example H-2

Preparation of

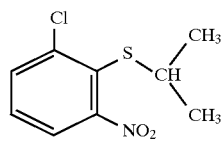

Method a): Prior-art process

The procedure is as described in Example H-1, except that 61 g of isopropylmercaptan are used instead of tert-butylmercaptan, whereupon 175 g of the product of m.p. 64°–67° C. are obtained (yield>95%).

Method b): Process according to the present invention 80.1 g of isopropylmercaptan are metered at 65°–70° C. to a mixture of 195.5 g of 2,3-dichloronitrobenzene, 3.22 g of tetrabutylammonium bromide, 157.3 g of 30% sodium hydroxide solution and 120 g of water. Stirring is thereupon continued for one hour at 65°–70° C., 100 g of isopropanol are added to the reaction mixture at 70° C., and the aqueous bottom phase is separated off. The organic phase is washed with dilute aqueous hydrochloric acid to a pH of 5–7 and cooled to 0° C., and the product which has crystallized out is filtered off and washed with approximately 40 g of isopropanol. This gives 225 g of product, m.p. 65°–67° C. (yield 95% of theory).

Example H-3

Preparation of

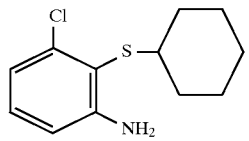

345 g of sodium sulfide hydrate in 500 ml of water are added in the course of 2 hours at 80°–82° C. to 401.3 g of 1-chloro-2-cyclohexylthio-3-nitrobenzene in 560 ml of isopropanol. After the mixture has been stirred at 82° C. for 3 hours, it is cooled to 20°–25° C., and the aqueous phase is separated off. The organic phase is washed using 200 ml of 25% sodium chloride solution. The organic phase is subsequently concentrated and distilled at 180° C./0.2 torr. Yield: 278.4 g (77%) of a yellow oil.

Example H-4

Preparation of

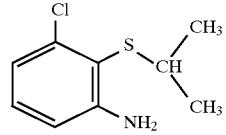

335 g of 1-chloro-2-isopropylthio-3-nitrobenzene (from Example H-2) are hydrogenated in 900 g of methanol at 35°–40° C./5 bar in the presence of 27.5 g of Raney nickel (as an aqueous suspension). After the uptake of hydrogen has ended, the mixture is cooled to room temperature, Raney nickel is filtered off, and the solvent is distilled off on a rotary evaporator. The residue (crude product) is employed directly for the subsequent step or distilled at 90°–100° C./0.05 mbar, yield: 272 g (95%).

Reaction times a) with educt which has been prepared in accordance with the prior art: Example H-2, method a): 3.5 hours b) with educt which has been prepared by the process according to the invention: Example H-2, method b): 0.5 hours.

Example H-5

Preparation of

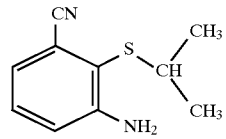

H-5(1): 60.5 g of 3-chloro-2-isopropylthioaniline (from Example H-4), 26.9 g of copper(I) cyanide and 26.1 g of pyridine are heated at 190° C. for 7 hours. 100 ml of acetonitrile are added dropwise with evaporative cooling, and 7 ml of water are subsequently added followed by 21.5 g of sodium sulfide hydrate, a little at a time. After the mixture has been stirred at 80° C. for 4 hours, it is cooled and filtered, and the filtrate is concentrated. After distillation at 70°–120° C./0.05 torr, 200 ml of hexane are added and the mixture is filtered. Yield: 22.7 g (40%) of 3-amino-2-isopropylthiobenzonitrile of m.p. 82° C.

H-5(2): 202 g of 3-chloro-2-isopropylthioaniline (from Example H-4), 134 g of copper(I) cyanide and 140 g of 3-methylpyridine are stirred at 190° C. for 9 hours. 200 g of methyl ethyl ketone, 60 g of sodium sulfide and 10 g of water are then added, the mixture is stirred, the salts are filtered off, and the filtrate is concentrated. The residue, which contains product and educt, is distilled at 70°–120° C./0.05 torr, and the distillate is crystallized from methylcyclohexane. This gives 125 g of product (65% of theory); the educt (20% of theory) remains in the mother liquor and can be recycled.

Example H-6
Preparation of the catalyst $Ni^{(o)}(PPh_3)_4$ 47.5 g of nickel chloride hexahydrate are introduced into 1,000 g of dimethylformamide and the mixture is stirred vigorously. Thereupon 209.8 g of triphenylphosphine are introduced. 150 g of DMF are distilled off, and 22 g of manganese powder are added under an inert atmosphere (nitrogen). The mixture is stirred at 50° C. for 1.5 hours, during which time the colour of the solution changes from deep blueish green via green to reddish brown. The catalyst is now ready for use without having to be isolated.

Example H-7
Preparation of 3-amino-2-isopropylthiobenzonitrile using separately prepared $Ni(PPh_3)_2Cl_2+2PPh_3$ as the catalyst 5 ml of DMF are added to 327 mg of nickel(II) bistriphenylphosphine chloride, 82 mg of manganese powder and 262 mg of triphenylphosphine under an inert atmosphere and the mixture is stirred at 50° C. for 45 minutes. 1 g of 3-chloro-2-isopropylthioaniline and 358 mg of potassium cyanide are subsequently added. The mixture is stirred at 50° C. for 17 hours. After 15 ml of toluene and 10 ml of water have been added, the mixture is clarified by filtration. 100 ml of toluene are added and the mixture is washed using 80 ml of water. The organic phase is concentrated and the residue chromatographed over silica gel (hexane/ethyl acetate=4:1). This gives 0.72 g of colourless crystals (yield: 76%).

Example H-8
Preparation of 3-amino-2-isopropylthiobenzonitrile using the catalyst prepared as described in Example H-6

201.5 g of 3-chloro-2-isopropylthioaniline are added to the catalyst mixture obtained in Example H-8. 51.5 g of sodium cyanide are added at 50° C. with vigorous stirring. The reaction is checked every 3 hours. After a maximum of 24 hours, the reaction has ended. The reaction mixture is concentrated in vacuo. The residue is treated with 1 liter of methyl ethyl ketone and 1 liter of water, stirred vigorously and filtered. The solution is left to stand to allow the phases to separate. The organic phase which has been separated off is concentrated and the residue treated with 800 ml of cyclohexane at 50° C. After solids have dissolved, it is cooled to 0° C. and seeded. 117 g (61%) of white crystals are obtained.

Example H-9
Preparation of 3-amino-2-isopropylthiobenzonitrile 6 liters of dimethylformamide are added to 50 g of nickel chloride dihydrate, 200 g of BPPFA (1,1'-bisdiphenylphosphine-1-(dimethylaminoethyl)ferrocene) and 49 g of manganese powder, and the mixture is stirred at 50° C. for 2 hours under an inert atmosphere. A brown suspension forms. 1,200 g of 3-chloro-2-isopropylthioaniline and 430 g of KCN are added to the suspension and the mixture is stirred for 16 hours at 50° C. After working up, white crystals of m.p. 82° C. are obtained in a yield of approximately 90%.

Example H-10
Preparation of

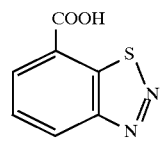

28.8 g of 3-amino-2-isopropylthiobenzonitrile are added to a mixture of 30.6 g of 96% sulfuric acid and 8.6 g of water at 120° C. After the mixture has been heated at 120° C. for 2 hours and at 149° C. for a further 2 hours, 3-amino-2-isopropylthiobenzoic acid, which precipitates in the form of the sulfate, is obtained in virtually quantitative yield. When cold, the suspension is treated with 150 ml of water and 80 ml of isopropanol. The mixture is cooled down to 0° C., and a solution of 20.8 g of sodium nitrite in 48.6 g of water is added dropwise in the course of 4 hours. After a further hour at 0° C., the mixture is treated with 10.6 g of acetamide in 20 ml of water are added and filtered. Yield: 23.4 g of white crystals (87%).

Example H-11
Preparation of

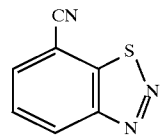

9.6 g of 3-amino-2-isopropylthiobenzonitrile in 20 ml of butanol are added dropwise at 15° C. in the course of 3 hours to 7 g of pentyl nitrite, 40 ml of butanol and 1.1 g of concentrated hydrochloric acid. After the mixture has been stirred for a further 3 hours, 0.6 g of acetamide and 100 ml of water are added. The organic phase is separated off and concentrated in vacuo. This gives 8.3 g of 7-cyanobenzothiadiazole in the form of white crystals (yield:>97%); m.p. 114°–117° C.

Example H-12
Preparation of

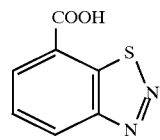

8.1 g of 7-cyanobenzothiadiazole in 80 g of butanol are treated with 16.8 g of 5% potassium hydroxide solution and the mixture is heated at 195° C. for 3 hours. During these 3 hours, the 7-carboxamide-benzothiadiazole precipitates and later redissolves as the salt of the acid. After the mixture has cooled to 40°–50° C., 200 ml of water are added and the phases are separated. The aqueous phase is acidified using hydrochloric acid and is filtered. Yield: 8 g of benzothiadiazole-7-carboxylic acid of an m.p. of about 230° C. (88%).

Example H-13
Preparation of

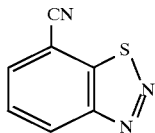

9.6 g of 3-amino-2-isopropylthiobenzonitrile in the form of a suspension in 80 ml of water and 14.3 g of 32% hydrochloric acid are treated at 15° C. in the course of 2 hours with a solution of 3.45 g of sodium nitrite in 20 ml of water. After stirring has been continued for 2 hours at 15° C., 1.5 g of acetamide are added, and the product which has precipitated is filtered off with suction, washed with water and dried. Yield: 7.7 g (93%) of white crystals of m.p. 116°–119° C.

Example H-14
Preparation of

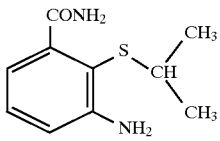

20.2 g of 3-chloro-2-isopropylthioaniline, 10.8 g of copper(I) cyanide, 0.7 g of copper(II) chloride and 3.2 g of pyridine are heated at 160° C. for 22 hours. After this time, 50 ml of butanol and 11.2 g of KOH are added and the mixture is heated at 110° C. for 6 hours. 4 ml of water are subsequently added and the mixture is stirred for a further 18 hours at 110° C. When cold, the mixture is treated with 100 ml of water, filtered, and the liquid phases are washed using 50 ml of methyl isobutyl ketone and 50 ml of water and acidified using 20 g of concentrated hydrochloric acid. After phase separation, the aqueous phase is rendered alkaline using 30% sodium hydroxide solution, and the precipitate is extracted using methyl isobutyl ketone. Filtration and concentration of the methyl isobutyl ketone phase yield 4.2 g (20%) of a brown oil which solidifies later; m.p. 93°–97° C.

Example 15
Preparation of

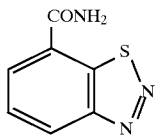

2.1 g of 3-amino-2-isopropylthiobenzamide (from Example H-11), 20 ml of water and 5.7 g of concentrated hydrochloric acid are treated with 0.7 g of sodium nitrite in 4 ml of water at 10° C. in the course of 45 minutes. After one hour at 10° C., 1 g of sulfamic acid is added, and the mixture is subsequently rendered alkaline using sodium hydroxide solution. After filtration and washing with water, the mixture is dried. Yield: 1.2 g of crystals (67%) of m.p.>300° C.

Example H-16
Preparation of

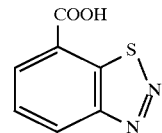

An aqueous solution of 140 g of sodium nitrite is metered at up to 0°–5° C. to a suspension of 192 g of 3-amino-2-isopropylthiobenzonitrile in 110 g of sulfuric acid and 500 g of water. After the reaction, the mixture is extracted using toluene, and the organic phase together with 360 g of 30% sodium hydroxide solution is stirred at 60° C. for 4 hours. The toluene phase (which contains the secondary products) is separated off, the aqueous phase is acidified using hydrochloric acid, and the product which has crystallized out during this process is filtered off. Yield: 171 g (95% of theory).

What is claimed is:

1. A process for the preparation of substituted 3-aminobenzonitriles of the formula I

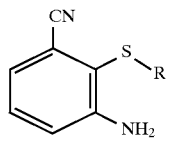

in which:

R is hydrogen or $C_1$–$C_{12}$alkyl, $C_3$–$C_8$cycloalkyl, $COR_1$, $C_1$–$C_8$alkoxyalkyl,
$C_1$–$C_6$hydroxyalkyl, $C_1$–$C_8$aminoalkyl, $C_1$–$C_8$alkyl-NH ($C_1$–$C_4$alkyl),
$C_1$–$C_8$alkyl-N($C_1$–$C_4$alkyl)$_2$ or substituted or unsubstituted benzyl; and $R_1$ is $C_1$–$C_8$alkyl, $C_3$–$C_8$cycloalkyl or phenyl;

which comprises reacting, in a solvent at above 30° C., a substituted 3-aminochlorobenzene of the formula II

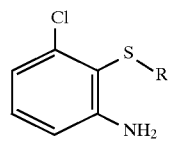

in which R is as defined for formula I, with a cyano-donating reagent selected from amongst a) CuCN or potassium cyanoferrate(II) (=$K_4$[Fe(CN)$_6$]) or calcium cyanoferrate(II) (=$Ca_2$[Fe(CN)$_6$]), in the presence of a complexing agent; or b) any Cu(I) salt together with an alkali metal cyanide in the presence of a complexing agent; or c) alkali metal cyanide, HCN, Ni(CN)$_2$ or tetramethylsilyl cyanide, or ketone HCN adduct or aldehyde HCN adduct, in the presence of a catalyst $M_3$[Co$^+$(CN)$_4$]$^{3-}$, or Pd°—$L_n$ or preferably Ni°—$L_n$ or a three-way mixture composed of NiL$_2$Hal$_2$, excess L and a reducing agent, M being an alkali metal, L being a ligand and n being 2 to 4.

2. A process according to claim 1, wherein the reaction is carried out with a) an equimolar (based on II) amount of CuCN or potassium cyanoferrate(II) (=$K_4$[Fe(CN)$_6$]) or calcium cyanoferrate(II) (=Ca$_2$[Fe(CN)$_6$]), in the presence of pyridine, methylpyridine, dimethylpyridine, trimethylpyridine, quinoline, dimethylaniline, acetonitrile, DMSO, benzonitrile, DMF or tetramethylurea; or b) any Cu(I) salt together with at least equimolar or greater (based on II) amounts of alkali metal cyanide, in the presence of pyridine, methylpyridine, dimethylpyridine, trimethylpyridine, quinoline, dimethylaniline, acetonitrile, DMSO, benzonitrile, DMF or tetramethylurea; or c) at least equimolar (based on II) amounts of alkali metal cyanide, HCN, Ni(CN)$_2$ or tetramethylsilyl cyanide, or keton HCN adduct or aldehyde HCN adduct, in the presence of a catalyst M$_3$[Co$^+$(CN)$_4$]$^{3-}$, or Pd$^\circ$—L$_n$ or, preferably, Ni$^\circ$—L$_n$, or a three-way mixture composed of NiL$_2$Hal$_2$, excess L and a reducing agent, M being an alkali metal, L a ligand and n 2 to 4.

3. A process according to claim 1, wherein the complexing agent in reaction a) or b) is a nitrogen-containing, electron-donating compound.

4. A process according to claim 3, wherein the complexing agent is pyridine, quinoline or isoquinoline, which are unsubstituted or mono- to trisubstituted by C$_1$–C$_4$alkyl, C$_1$–C$_4$alkoxy, amino, C$_1$–C$_4$alkylamino or (C$_1$–C$_4$alkyl)$_2$ amino.

5. A process according to claim 4, wherein the complexing agent is pyridine which is unsubstituted or mono- to trisubstituted by methyl, or is quinoline.

6. A process according to claim 5, wherein the complexing agent is pyridine or 3-methylpyridine.

7. A process according to claim 1, wherein reaction a) is carried out using CuCN.

8. A process according to claim 1, wherein reaction b) is carried out using alkali metal cyanide.

9. A process according to claim 1, wherein reaction c) is carried out using a catalyst of the formula Ni$^\circ$—L$_n$ in which L is triphenylphosphine and n is 2 to 4, or a catalyst of the formula Ni$^\circ$—L$_2$ in which L$_2$ is (1,1'-bisdiphenylphosphine-1-(dimethylaminoethyl)ferrocene).

10. A process according to claim 1, wherein the catalyst in reaction c) is prepared in situ.

11. A process according to claim 1, wherein the reaction is carried out at 50° to 350° C.

12. A process according to claim 1, wherein reaction a) or b) is carried out at 150° to 250° C.

13. A process according to claim 1, wherein reaction c) is carried out at 30° to 150° C.

14. A process according to claim 1, wherein, in reaction a), at least equimolar amounts of the complexing agent, based on Cu or Fe, is used as the solvent.

15. A process according to claim 14, wherein pyridine which is unsubstituted or mono- to trisubstituted by methyl, or quinoline, are used as the solvent.

16. A process according to claim 15, wherein pyridine or 3-methylpyridine are used as the solvent.

17. A compound of the formula I

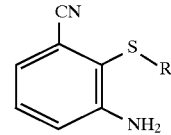

in which:

R is hydrogen or C$_1$–C$_{12}$alkyl, C$_3$–C$_8$cycloalkyl, COR$_1$, C$_1$–C$_8$alkoxyalkyl, C$_1$–C$_6$hydroxyalkyl, C$_1$–C$_8$aminoalkyl, C$_1$–C$_8$alkyl-NH (C$_1$–C$_4$alkyl), C$_1$–C$_8$alkyl-N(C$_1$–C$_4$alkyl)$_2$ or a substituted or unsubstituted benzyl group; and R$_1$ is C$_1$–C$_8$alkyl, C$_3$–C$_8$cycloalkyl or phenyl.

18. A compound of the formula I according to claim 17 in which R is sec-C$_3$–C$_6$alkyl or tert-C$_4$–C$_6$alkyl or C$_5$–C$_6$cycloalkyl.

19. A compound of the formula I according to claim 18 in which R is isopropyl, tert-butyl or cyclohexyl.

* * * * *